(12) United States Patent
Denda et al.

(10) Patent No.: US 11,530,983 B2
(45) Date of Patent: Dec. 20, 2022

(54) SENSOR MODULE

(71) Applicant: SHINKO ELECTRIC INDUSTRIES CO., LTD., Nagano (JP)

(72) Inventors: Tatsuaki Denda, Nagano (JP); Yuji Furuta, Nagano (JP)

(73) Assignee: SHINKO ELECTRIC INDUSTRIES CO., LTD., Nagano (JP)

( * ) Notice: Subject to any disclaimer, the term of this patent is extended or adjusted under 35 U.S.C. 154(b) by 0 days.

(21) Appl. No.: 17/341,646

(22) Filed: Jun. 8, 2021

(65) Prior Publication Data

US 2021/0396658 A1    Dec. 23, 2021

(30) Foreign Application Priority Data

Jun. 23, 2020 (JP) .............................. JP2020-108087

(51) Int. Cl.
*G01N 21/3504* (2014.01)
*G01N 33/497* (2006.01)
*G02B 5/20* (2006.01)

(52) U.S. Cl.
CPC ....... *G01N 21/3504* (2013.01); *G01N 33/497* (2013.01); *G02B 5/20* (2013.01)

(58) Field of Classification Search
CPC ..... G01N 21/3504; G01N 33/497; G02B 5/20
See application file for complete search history.

(56) References Cited

U.S. PATENT DOCUMENTS

| 5,789,660 | A | 8/1998 | Kofoed et al. |
| 9,001,331 | B2 * | 4/2015 | Martin ............... G01N 21/3504 |
| | | | 356/437 |
| 2007/0225612 | A1 | 9/2007 | Mace et al. |
| 2016/0231244 | A1 * | 8/2016 | Camargo ........... G01N 21/0303 |
| 2019/0200899 | A1 | 7/2019 | Yoshida |

FOREIGN PATENT DOCUMENTS

| CN | 106999845 A | * | 8/2017 | ............... A61L 9/20 |
| JP | 2003345268 A | * | 12/2003 | |
| JP | 2010-517635 | | 5/2010 | |
| JP | 2017-184993 | | 10/2017 | |

* cited by examiner

*Primary Examiner* — Kiho Kim
(74) *Attorney, Agent, or Firm* — IPUSA, PLLC (57) ABSTRACT

A sensor module for measuring a concentration of a gas by utilizing changes in an amount of absorbed light includes a light emitting device and a light receiving device configured to receive light emitted by the light emitting device, wherein the light emitting device and the light receiving device are disposed to face each other across a gap, wherein the light emitting device and the light receiving device are positioned such as to be exposed to the gas, and the gap forms part of a flow pathway of the gas, and wherein the gap is greater than or equal to 0.2 mm and less than or equal to 1.0 mm.

10 Claims, 8 Drawing Sheets

SENSOR MODULE

CROSS-REFERENCE TO RELATED APPLICATIONS

The present application is based on and claims priority to Japanese Patent Application No. 2020-108087 filed on Jun. 23, 2020, with the Japanese Patent Office, the entire contents of which are incorporated herein by reference.

FIELD

The disclosures herein relate to a sensor module.

BACKGROUND

As known in the art, an non-dispersive infrared (NDIR) method may be used to monitor biological information. This method utilizes the phenomenon in which infrared rays emitted from an infrared radiation source are absorbed by gas molecules, thereby making it possible to measure various gases. Utilizing this method enables the realization of a sensor module that detects the concentration of carbon dioxide contained in the breath of a subject, for example.

The sensor module as noted above needs to converge light from an infrared radiation source by use of a mirror and a lens, for example, in order to detect a weak infrared ray, which makes it difficult to achieve size reduction.

Accordingly, there may be a need to reduce the size of a sensor module for measuring gas concentration.
[Patent Document 1] Japanese National Publication of International Patent Application No. 2010-517635
[Patent Document 2] Japanese Laid-open Patent Publication No. 2017-184993

SUMMARY

According to an aspect of the embodiment, a sensor module for measuring a concentration of a gas by utilizing changes in an amount of absorbed light includes a light emitting device and a light receiving device configured to receive light emitted by the light emitting device, wherein the light emitting device and the light receiving device are disposed to face each other across a gap, wherein the light emitting device and the light receiving device are positioned such as to be exposed to the gas, and the gap forms part of a flow pathway of the gas, and wherein the gap is greater than or equal to 0.2 mm and less than or equal to 1.0 mm.

The object and advantages of the embodiment will be realized and attained by means of the elements and combinations particularly pointed out in the claims. It is to be understood that both the foregoing general description and the following detailed description are exemplary and explanatory and are not restrictive of the invention, as claimed.

DESCRIPTION OF EMBODIMENTS

In the following, embodiments will be described by referring to the accompanying drawings. In these drawings, the same elements are referred to by the same references, and a duplicate description thereof may be omitted.

First Embodiment (Configuration of Sensor Module)

Figure 1A:
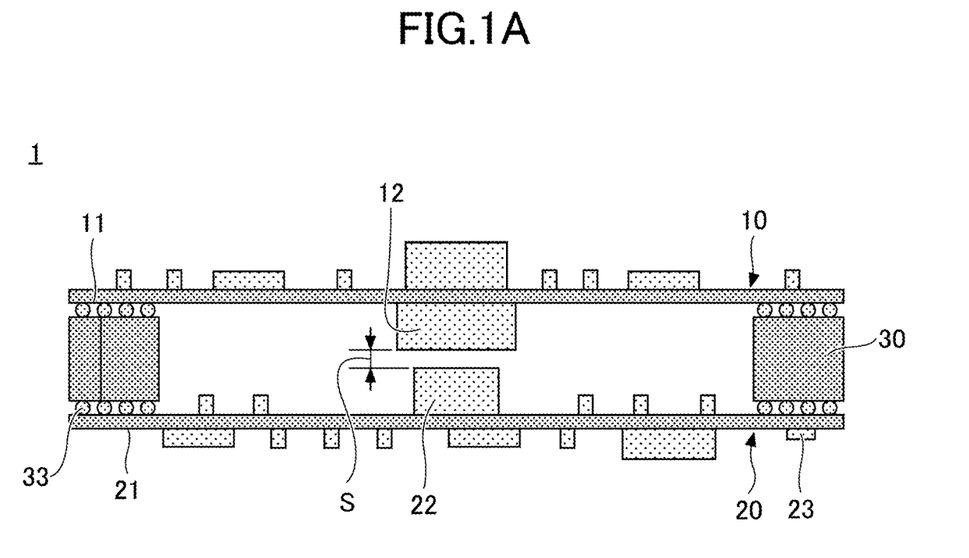
FIGS. 1A and 1B are drawings illustrating an example of a sensor module according to a first embodiment.
Figure 1B:
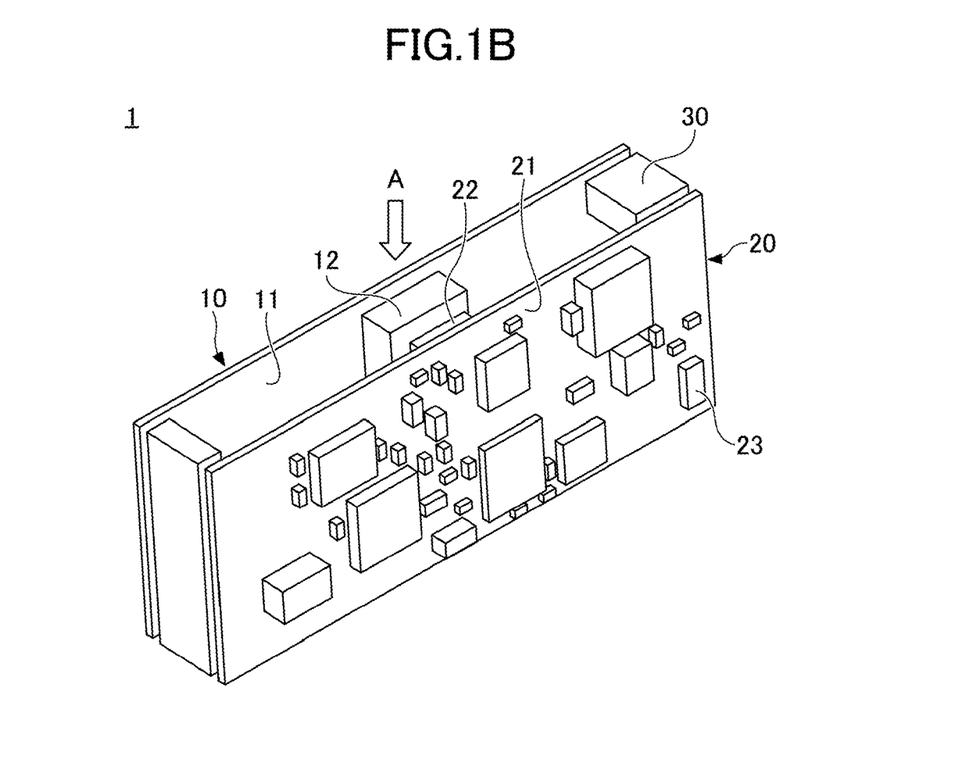

FIGS. 1A and 1B are drawings illustrating an example of a sensor module 1 according to a first embodiment. FIG. 1A is a side elevation view of the sensor module 1 providing a view of the intake side thereof. FIG. 1B is an axonometric view of the sensor module 1 that is positioned with the intake side facing upward. The sensor module 1 receives breath in the direction indicated by an arrow A in FIG. 1B.

As illustrated in FIGS. 1A and 1B, the sensor module 1 includes a light emitting device mounting substrate 10, a light receiving device mounting substrate 20, and an intermediate substrate 30. The sensor module 1 has the function to measure the concentration of a predetermined gas by utilizing changes in the amount of absorbed light. In the present embodiment, the sensor module 1 may be a capnometer, for example. A capnometer is a device that measures the concentration of carbon dioxide contained in a person's breath by utilizing the fact that the amount of infrared light absorption changes in response to the concentration of carbon dioxide.

The light emitting device mounting substrate 10 includes a substrate 11 and a light emitting device 12. The light emitting device mounting substrate 10 and the light receiving device mounting substrate 20 are disposed to face each other with the intermediate substrate 30 disposed therebetween.

The substrate 11 may be a rigid substrate such as a resin substrate (e.g., a glass epoxy substrate), a silicon substrate, or a ceramic substrate, for example. Interconnects and pads made of copper or the like are formed on both sides of the substrate 11. The interconnects may additionally or alternatively be provided in an inner layer of the substrate 11. Namely, the substrate 11 may be a multilayer interconnect substrate. The light emitting device 12 is mounted on that surface of the substrate 11 which faces the light receiving device mounting substrate 20. The light emitting device 12 may be a light emitting diode (LED), for example.

It is preferable for the light emitting device 12 to be mounted near the intake side (i.e., the same side as the arrow A in FIG. 1B) for the purpose of reducing the influence of external disturbance noise to achieve higher measurement accuracy. The light emitting device 12, which is mounted on that surface of the substrate 11 which faces the light receiving device mounting substrate 20, may be mounted substantially at the center of the substrate 11 near the intake side. Light reflected at the substrate 11 functions as external disturbance noise. In order to reduce light reflection on the substrate 11, it may be preferable that the surface of the substrate 11 on which the light emitting device 12 is mounted is covered with a black resist.

The light receiving device mounting substrate 20 includes a substrate 21, a light receiving device 22, and an antenna 23. The light receiving device mounting substrate 20 and the light emitting device mounting substrate 10 are disposed to face each other with the intermediate substrate 30 disposed therebetween. The space between the light emitting device mounting substrate 10, the light receiving device mounting substrate 20, and the intermediate substrate 30 serves as a gas flow pathway.

The substrate 21 may be a rigid substrate such as a resin substrate (e.g., a glass epoxy substrate), a silicon substrate, or a ceramic substrate, for example. Interconnects and pads made of copper or the like are formed on both sides of the substrate 21. The interconnects may additionally or alternatively be provided in an inner layer of the substrate 21. Namely, the substrate 21 may be a multilayer interconnect substrate. The light receiving device 22 is mounted on that surface of the substrate 21 which faces the light emitting device mounting substrate 10. The light receiving device 22 may be a photodiode (PD), for example.

The light receiving device 22 is disposed at such a suitable position as to receive the light emitted by the light emitting device 12. Specifically, the light receiving device 22 is disposed opposite the light emitting device 12 across a gap S. Namely, the light emitting device mounting substrate 10 and the light receiving device mounting substrate 20 are spaced from each other such that the light emitting device 12 and the light receiving device 22 face each other across the gap S. The light emitting device 12 and the light receiving device 22 are positioned such as to be exposed to gas, and the space S forms part of the gas flow pathway.

It is preferable for the light receiving device 22 to be mounted near the intake side for the purpose of reducing the influence of external disturbance noise. The light receiving device 22, which is mounted on that surface of the substrate 21 which faces the light emitting device mounting substrate 10, may be mounted substantially at the center of the substrate 21 near the intake side. Light reflected at the substrate 21 functions as external disturbance noise. In order to reduce light reflection on the substrate 21, it may be preferable that the surface of the substrate 21 on which the light receiving device 22 is mounted is covered with a black resist.

The antenna 23 is mounted on the surface of the substrate 21 facing away from the light emitting device mounting substrate 10. The antenna 23 is an electronic component that enables the transmission and reception of radio waves between the sensor module 1 and an external device, thereby making it possible to transmit information about the concentration of carbon dioxide measured by the sensor module 1 to the external device, for example.

A number of electronic components (i.e., semiconductor components and passive components) in addition to the light emitting device 12, the light receiving device 22, and the antenna 23 are mounted on the light emitting device mounting substrate 10 and the light receiving device mounting substrate 20. Examples of the semiconductor components include a CPU (central processing unit), a ROM (read only memory), and a RAM (random access memory), a dedicated IC, and the like. Examples of passive components include a resistor, a capacitor, an inductor, a connector, and the like. These semiconductor components and electronic components may be mounted on either the light emitting device mounting substrate 10 or the light receiving device mounting substrate 20.

Figure 2A:
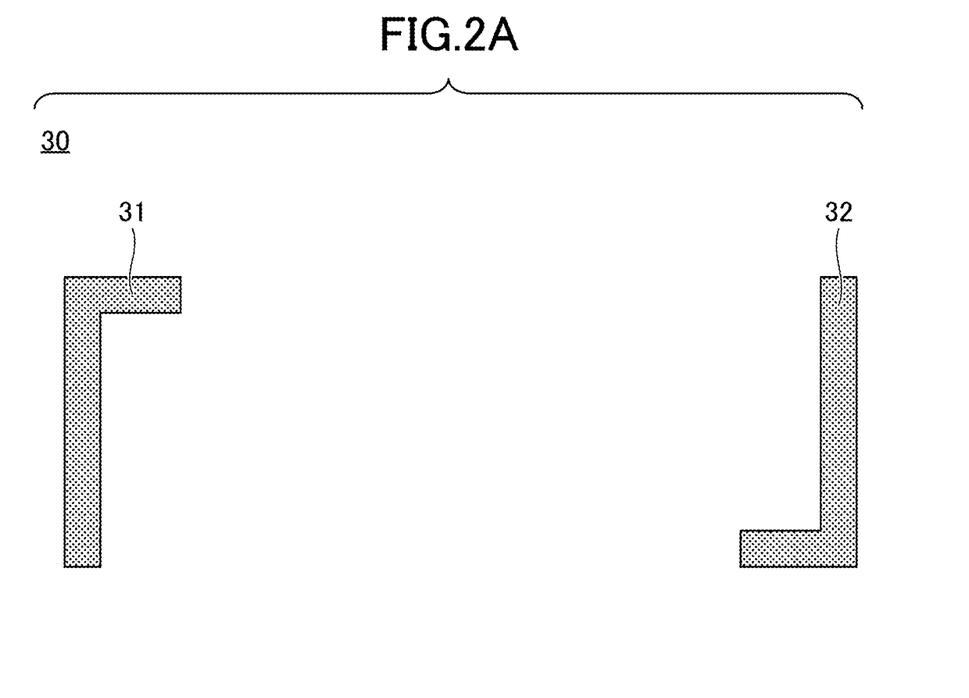
FIGS. 2A and 2B are drawings illustrating an example of the intermediate substrates of the sensor module according to the first embodiment.
Figure 2B:
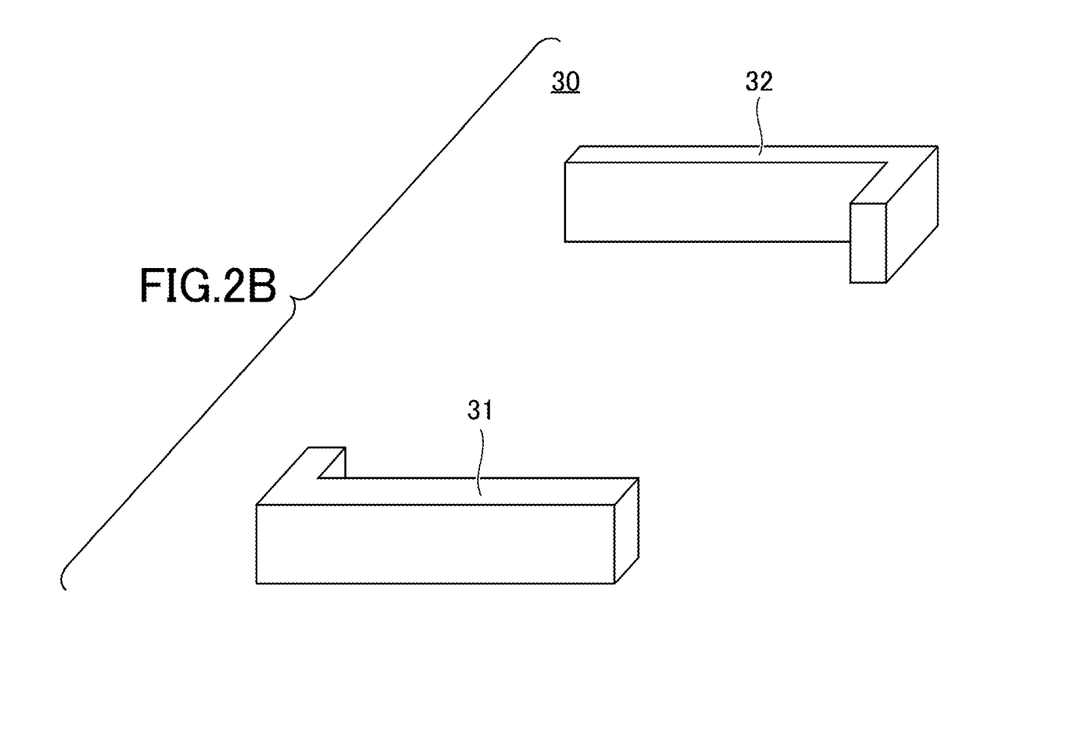

FIGS. 2A and 2B are drawings illustrating an example of the intermediate substrate of the sensor module according to the first embodiment. FIG. 2A illustrates a plan view, and FIG. 2B illustrates an oblique view.

As illustrated in FIGS. 2A and 2B, the intermediate substrate 30 includes two L-shaped substrates 31 and 32 disposed opposite each other as viewed in the direction normal to the light emitting device mounting substrate 10. The substrate 31 and the substrate 32 are positioned further out than the positions at which the light emitting device 12 and the light receiving device 22 are mounted as viewed in the direction normal to the light emitting device mounting substrate 10, such as to form a point symmetric pattern, for example. Namely, the substrate 31 and the substrate 32 are positioned farther away from the center of the gas flow pathway than are the light emitting device 12 and the light receiving device 22.

The substrates 31 and 32, which are disposed between the light emitting device mounting substrate 10 and the light receiving device mounting substrate 20 facing each other, are bonded to an outer edge of each substrate via a conductive bonding material 33. Solder balls, copper core balls, resin core balls, or the like, for example, may be used as the conductive bonding material 33. The substrates 31 and 32 have interconnects disposed thereon. The light emitting device mounting substrate 10 and the light receiving device mounting substrate 20 are electrically connected to each other via the interconnects disposed on the substrates 31 and 32.

As described above, the substrates 31 and 32 and the conductive bonding material 33 are bonding members for bonding the light emitting device mounting substrate 10 and the light receiving device mounting substrate 20. The light emitting device mounting substrate 10 and the light receiving device mounting substrate 20 are disposed to face each other via the bonding members.

(Function of Sensor Module)

Figure 3:
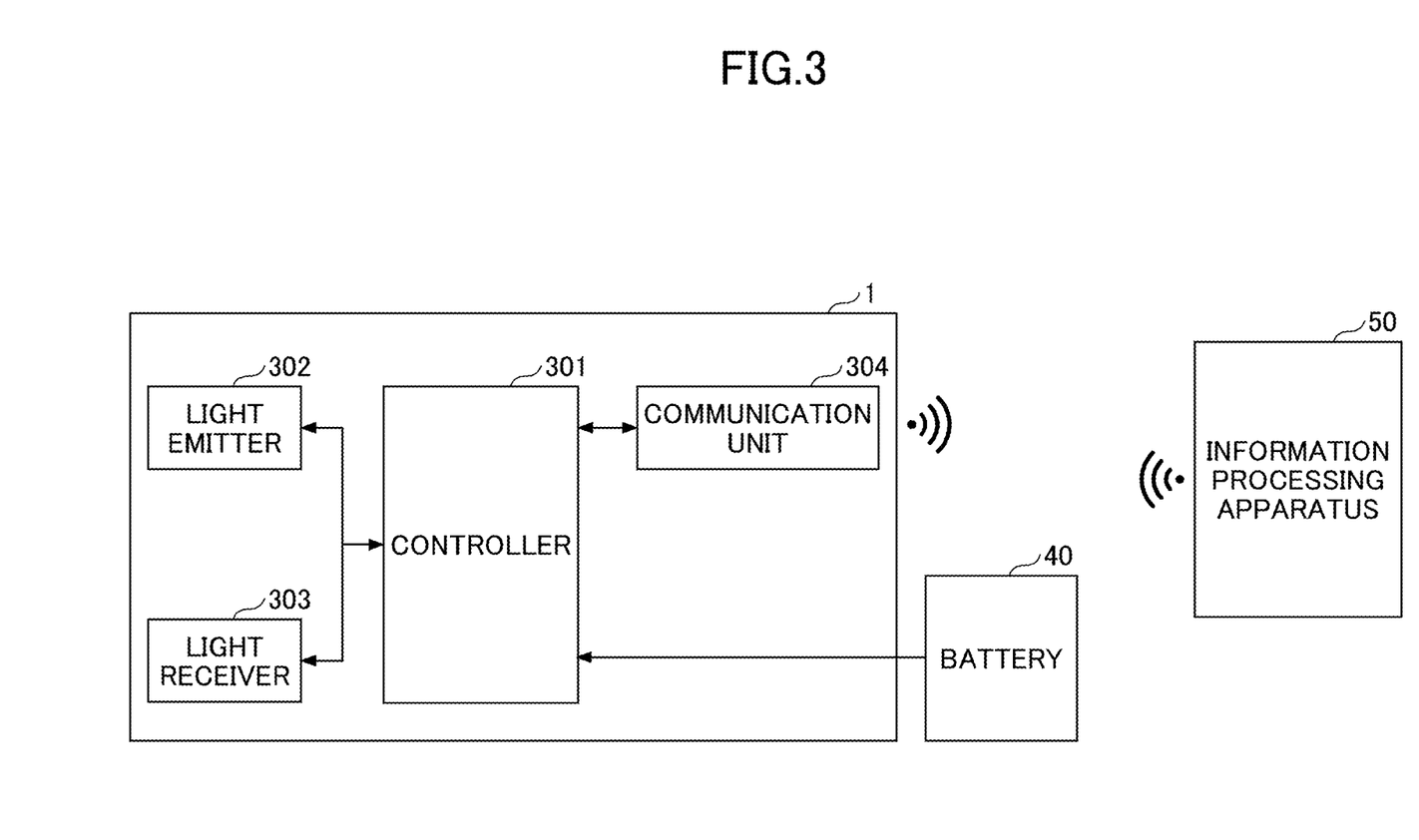
FIG. 3 is a drawing illustrating an example of the functional blocks of the sensor module according to the first embodiment.

FIG. 3 is a drawing illustrating an example of the functional blocks of the sensor module of the first embodiment. As illustrated in FIG. 3, the sensor module 1 includes, as functional blocks, a controller 301, a light emitter 302, a light receiver 303, and a communication unit 304. The sensor module 1 may include one or more other functional blocks as needed.

The controller 301 may include a CPU, a ROM, a RAM, a main memory, and the like, for example. In this case, various functions of the controller 301 may be provided by the CPU executing programs that are loaded from the ROM to the main memory. Alternatively, the controller 301 may be implemented solely as hardware. The controller 301 may operate by receiving power from a battery 40 disposed outside the sensor module 1.

The light emitter 302 has the function to emit light from the light emitting device 12 under the control of the controller 301. The light emitter 302 includes the light emitting device 12 and a drive circuit for driving the light emitting device 12, for example.

The light receiver 303 has the function to receive light emitted from the light emitter 302 and to convert the received light into an electrical signal. The light receiver 303 includes the light receiving device 22 and a drive circuit for driving the light receiving device 22, for example. Information received by and converted into the electrical signal by the light receiver 303 is transmitted to the CPU, for example.

The communication unit 304 has the function to enable the transmission and reception of information via wireless communication between the controller 301 and an information processing apparatus 50 disposed outside the sensor module 1. The information processing apparatus 50 may be a personal computer or a tablet terminal, for example. The communication unit 304 may be implemented as a communication device (not shown) and an antenna 23, for example. The communication unit 304 may transmit, to the information processing apparatus 50, data indicative of carbon dioxide concentration calculated by the controller 301 based on the output of the light receiver 303, for example.

In the following, the theoretical principle of measuring carbon dioxide concentration will be described. Each molecule has a different resonance frequency, and absorbs light when being illuminated with light close to resonance. Carbon dioxide contained in breath has a resonance frequency of around 4.3 micrometers. Use of a light emitting device emitting light in a wavelength band around 4.3 micrometers allows infrared spectroscopy utilizing light absorption to detect carbon dioxide concentration.

Specifically, a light emitting device that emits light in a wavelength band around 4.3 micrometers is used as the light emitting device 12, and light is emitted from the light emitting device toward the light receiving device 22. Carbon dioxide entering the gap S between the light emitting device 12 and the light receiving device 22 absorbs light, so that the light intensity received by the light receiving device 22 decreases. The lower the concentration of carbon dioxide is, the higher the intensity of light received by the light receiving device 22 is, and the intensity of light received by the light receiving device 22 decreases as the concentration of carbon dioxide increases, which allows the concentration of carbon dioxide to be calculated based on the intensity of light received by the light receiving device 22.

Since the light emitted from the light emitting device 12 is divergent and not parallel, the intensity of light received by the light receiving device 22 decreases as the gap S widens. It is thus preferable to have the gap S as narrow as possible without causing the opposing surfaces of the light emitting device 12 and the light receiving device 22 to come in contact with each other. The gap S is preferably 0.2 mm or more and 1.0 mm or less, more preferably 0.2 mm or more and 0.8 mm or less, and particularly preferably 0.2 mm or more and 0.4 mm or less.

Use of the gap S less than or equal to 1 mm improves the detection accuracy of carbon dioxide concentration. Use of the gap S less than or equal to 0.8 mm further improves the detection accuracy of carbon dioxide concentration. Use of the gap S less than or equal to 0.4 mm particularly improves the detection accuracy of carbon dioxide concentration. It may be noted that it is difficult to make the gap S shorter than 0.2 mm in consideration of mounting accuracy of the light emitting device 12 and the light receiving device 22.

In the case of detecting carbon dioxide concentration, it suffices for the light emitting device 12 to be able to emit light only in a wavelength band around 4.3 micrometers. Light in other wavelength bands other than the noted band, even if emitted, would not be used in the measurement. From the viewpoint of improving the efficiency of light utilization to reduce power consumption, it is preferable for the spectrum of the light emitting device 12 to include a wavelength of 4.3 micrometers and have a full width at half maximum of 0.8 micrometers or less.

It suffices for the light receiving device 22 to have light sensitivity to a wavelength of 4.3 micrometers. However, from the viewpoint of reducing the reception of light serving as noise, the light receiving device 22 preferably includes a bandpass filter that allows the passage of a wavelength of 4.3 micrometers. The narrower the bandwidth is, the more preferable the filter is.

Figure 4A:
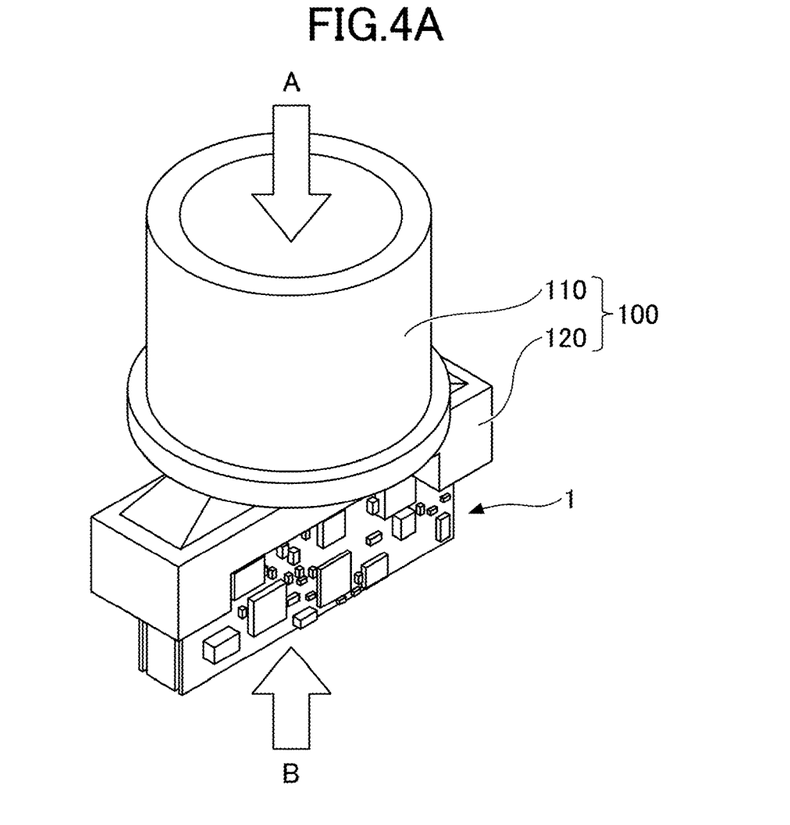
FIGS. 4A and 4B are drawings illustrating an example of the sensor module with an airway adapter attached thereto.
Figure 4B:
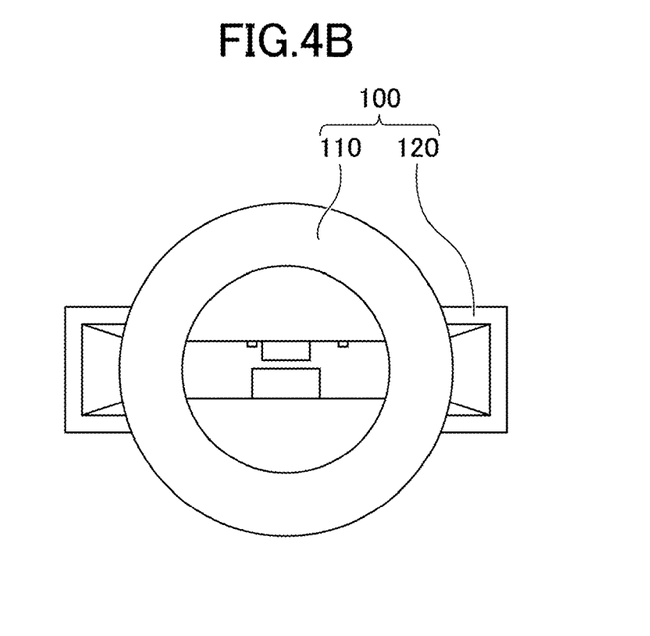

FIGS. 4A and 4B are drawings illustrating an example of the sensor module with an airway adapter attached thereto. FIG. 4A is an axonometric view, and FIG. 4B is a plan view (as viewed in the direction indicated by the arrow A).

As illustrated in FIGS. 4A and 4B, the sensor module 1 may be used with an airway adapter 100 attached thereto, for example. In FIGS. 4A and 4B, the arrow A indicates the intake side, and the arrow B indicates the exhaust side. The airway adapter 100 includes a gas flow pathway 110 and a mounting portion 120. The gas flow pathway 110 and the mounting portion 120 may be made as a unitary, seamless resin piece by molding.

The gas flow pathway 110 is a generally hollow cylindrical member that receives the breath of a subject. The mounting portion 120 is a generally hollow rectangular member for mounting the airway adapter 100 to the sensor module 1. The mounting portion 120 has one end thereof on the side indicated by the arrow A communicating with the gas flow pathway 110, and has the other end thereof on the side indicated by the arrow B provided with a frame-shaped opening into which the sensor module 1 is inserted. It is preferable for the mounting portion 120 to enclose at least the lateral sides of the portion in which the light emitting device 12 and the light receiving device 22 are disposed so as to prevent a gas from leaking to the outside. The mounting portion 120 may enclose the entire lateral sides of the light emitting device mounting substrate 10 and the light receiving device mounting substrate 20.

The breath of a subject injected into the gas flow pathway 110 from the side indicated by the arrow A passes through the hollow space inside the mounting portion 120 to reach the gap S formed between the light emitting device 12 and the light receiving device 22. With the light emitting device 12 emitting light, the intensity of light received by the light receiving device 22 changes in response to the concentration of carbon dioxide contained in the breath, which allows the concentration of carbon dioxide contained in the breath to be calculated based on the intensity of light received by the light receiving device 22.

It is preferable that the cross-sectional area of the gas flow pathway including the gap S is greater than or equal to 80 $mm^2$ when viewed from the intake side. With this arrangement, the subject can breathe without feeling shortage of breath. From the viewpoint of breath measurement, it is preferable that the cross-sectional area of the gas flow pathway including the gap S is less than or equal to 400 $mm^2$ when viewed from the intake side.

As was described above, the sensor module 1 measures the concentration of a gas present in the gap S by use of the light emitting device 12 and the light receiving device 22 disposed to face each other across the gap S, without using optical components such as a mirror and a lens. This arrangement enables the size reduction and thickness reduction of the sensor module 1. Further, the close proximity arrangement of the light emitting device 12 and the light receiving device 22 makes it possible to reduce the influence of external disturbance noise, thereby improving the accuracy of gas concentration measurement.

(First Variation of First Embodiment)

The first variation of the first embodiment is directed to an example of the sensor module in which the intermediate substrate has a different shape than in the first embodiment. In connection with the first variation of the first embodiment, descriptions of the same or similar constituent components as those of the previously provided descriptions may be omitted as appropriate.

Figure 5A:
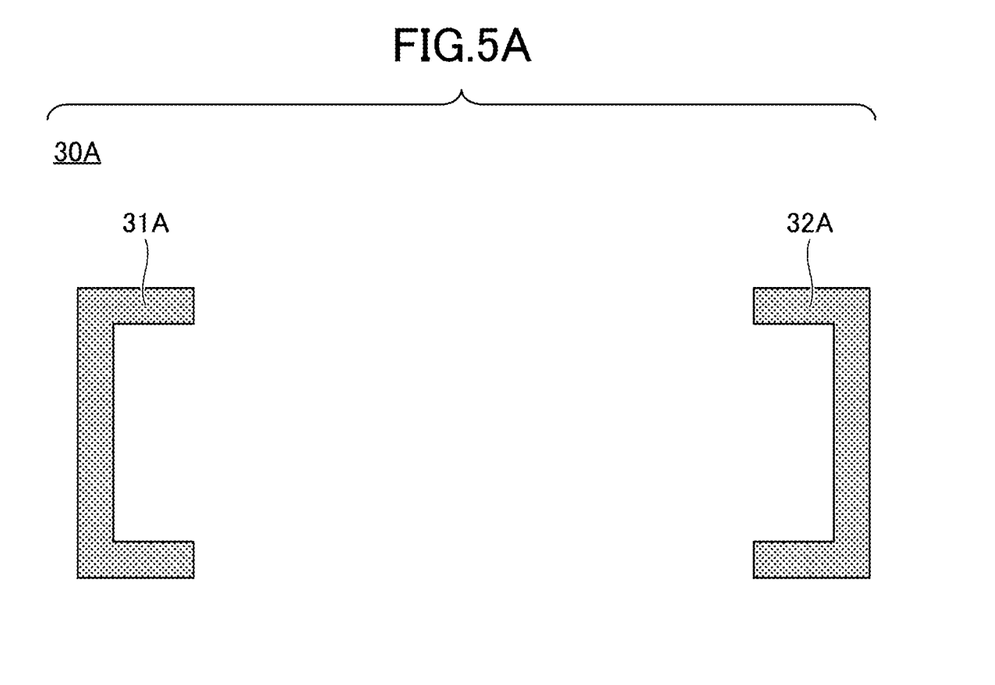
FIGS. 5A and 5B are drawings illustrating an example of the intermediate substrates of a sensor module according to a first variation of the first embodiment.
Figure 5B:
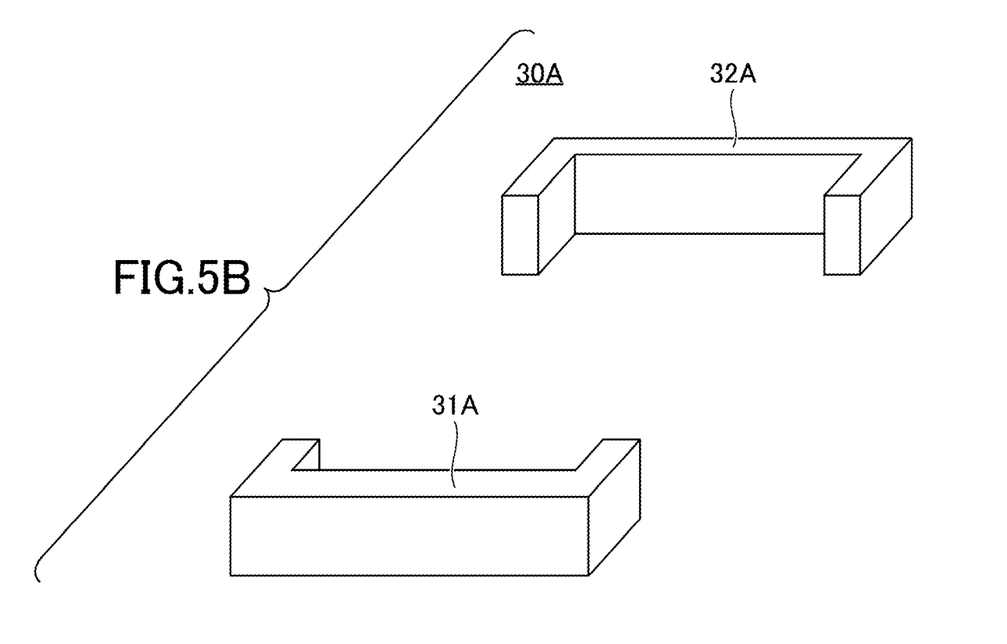
Figure 6A:
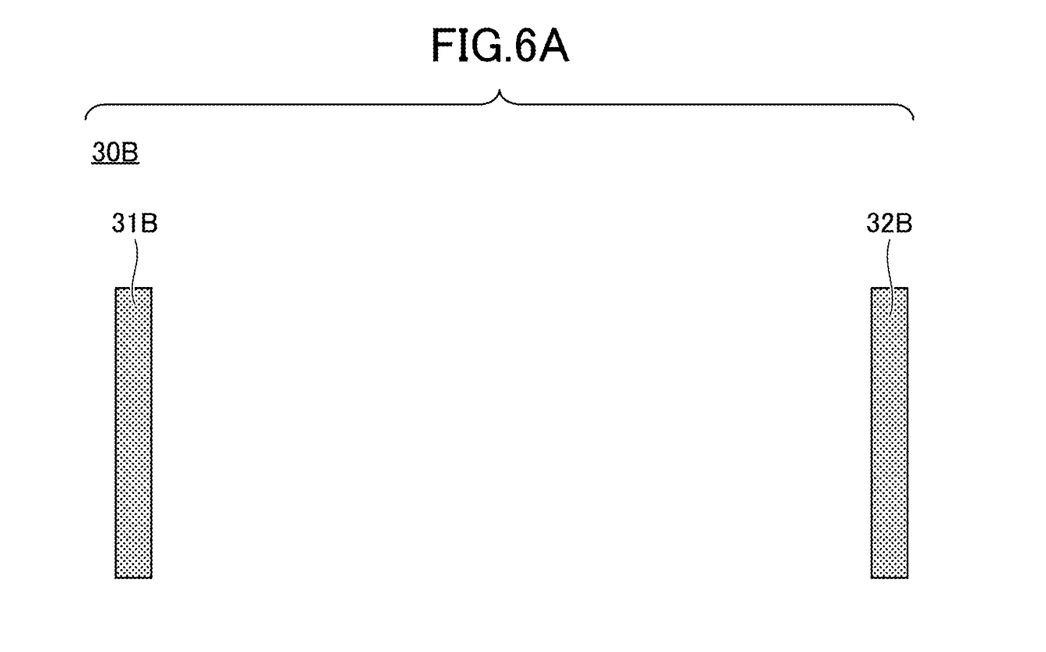
FIGS. 6A and 6B are drawings illustrating another example of the intermediate substrates of the sensor module according to the first variation of the first embodiment.
Figure 6B:
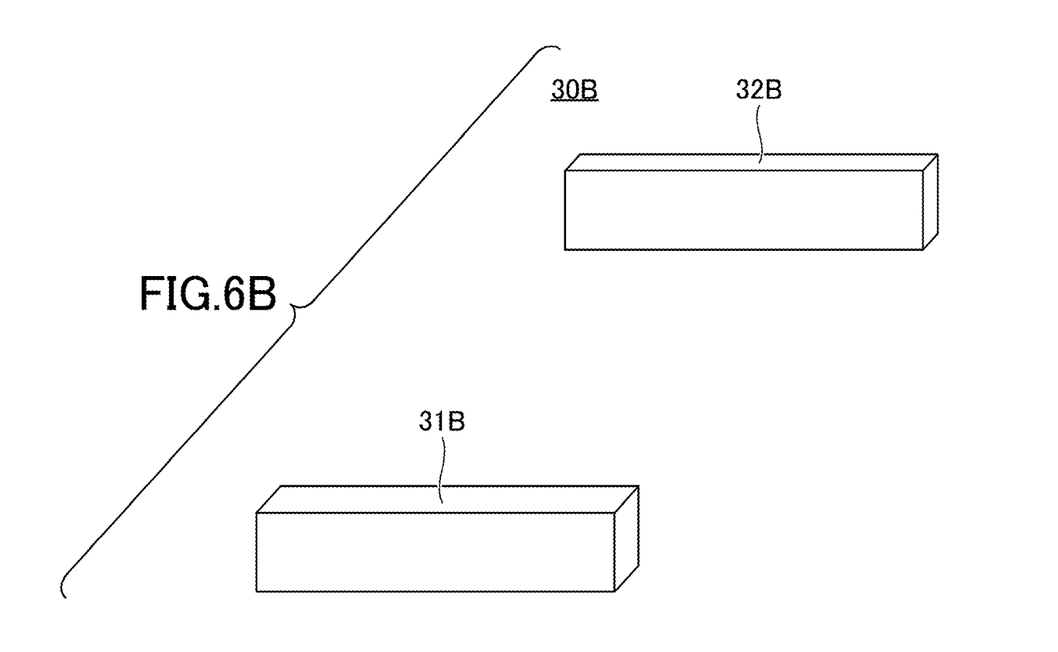

FIGS. 5A and 5B are drawings illustrating an example of the intermediate substrate of the sensor module according to the first variation of the first embodiment. FIG. 5A illustrates a plan view, and FIG. 5B illustrates an oblique view. FIGS. 6A and 6B are drawings illustrating another example of the intermediate substrate of the sensor module according to the first variation of the first embodiment. FIG. 6A illustrates a plan view, and FIG. 6B illustrates an oblique view.

In the first embodiment, the intermediate substrate 30 includes the L-shaped substrates 31 and 32 disposed opposite each other as viewed in the direction normal to the light emitting device mounting substrate 10. In contrast, an intermediate substrate 30A illustrated in FIGS. 5A and 5B may include square-bracket shaped substrates 31A and 32A disposed opposite each other as viewed in the direction normal to the light emitting device mounting substrate 10. Alternatively, an intermediate substrate 30B illustrated in FIGS. 6A and 6B may include I-shaped substrates 31B and 32B disposed opposite each other as viewed in the direction normal to the light emitting device mounting substrate 10.

It may be noted that the L-shaped substrates 31 and 32 are superior to the square-bracket shaped substrates 31A and 32A as they can provide a larger cross-sectional area for the gas flow pathway, and are also superior to the I-shaped substrates 31B and 32B as they can stand on their own at the time of assembling the sensor module.

Figure 7A:
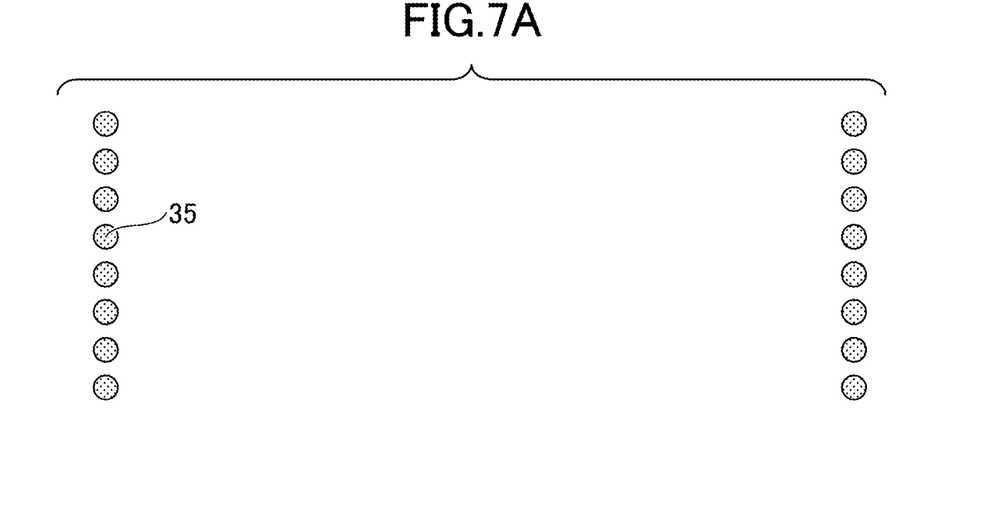
FIGS. 7A and 7B are drawings illustrating an example of the metal posts of the sensor module according to the first variation of the first embodiment.
Figure 7B:
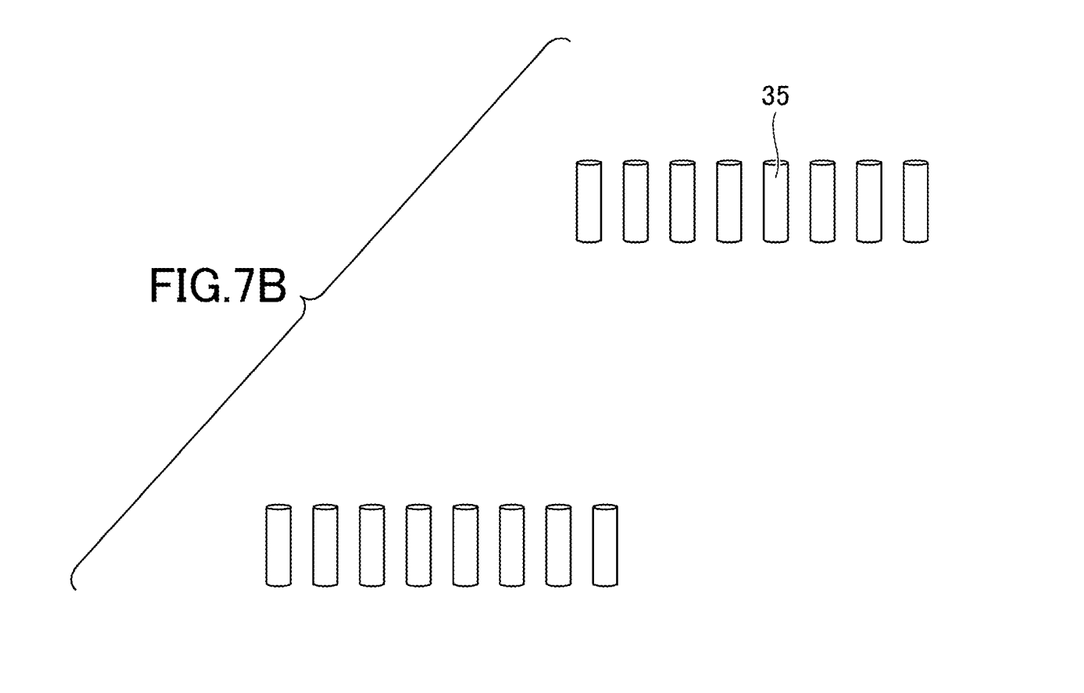

FIGS. 7A and 7B are drawings illustrating an example of metal posts of the sensor module according to the first variation of the first embodiment. FIG. 7A illustrates a plan view, and FIG. 7B illustrates an oblique view. As illustrated in FIGS. 7A and 7B, the bonding member interposed between the light emitting device mounting substrate 10 and the light receiving device mounting substrate 20 to serve as spacers may include metal posts 35 in place of intermediate substrates. The metal posts 35 are supposed to provide current paths between the light emitting device mounting substrate 10 and the light receiving device mounting substrate 20, and, thus, are suitably made of a material having excellent electrical conductivity, such as copper. The metal posts 35 are bonded to the light emitting device mounting substrate 10 and the light receiving device mounting substrate 20 with solder or the like, for example. The shape of the metal posts 35 may be a circular cylinder, an elliptic cylinder, a polygon cylinder, or the like, for example.

It may be noted that the bonding member interposed between the light emitting device mounting substrate 10 and the light receiving device mounting substrate 20 to serve as spacers may be connector components in place of intermediate substrates or metal posts.

(Second Variation of First Embodiment)

The second variation of the first embodiment is directed to an example in which a flexible substrate is used. In connection with the second variation of the first embodiment, descriptions of the same or similar constituent components as those of the previously provided descriptions may be omitted as appropriate.

Figure 8:
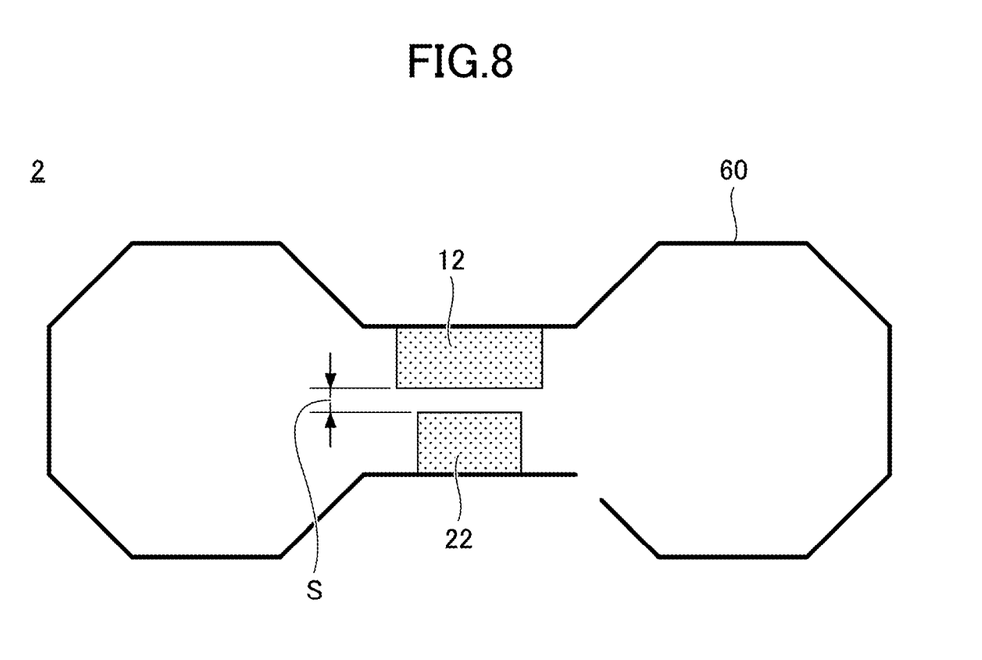
FIG. 8 is a drawing illustrating an example of a sensor module according to a second variation of the first embodiment.

FIG. 8 is a drawing illustrating an example of a sensor module according to the second variation of the first embodiment. FIG. 8 is a side elevation view of a sensor module 2 providing a view of the intake side thereof.

As illustrated in FIG. 8, the sensor module 2 has a flexible interconnect substrate 60. The light emitting device 12 and the light receiving device 22 are mounted on the same side of the interconnect substrate 60. The interconnect substrate 60 is bent such that the light emitting device 12 and the light receiving device 22 face each other across the gap S. A polyimide substrate or the like may be used as the interconnect substrate 60, for example. In FIG. 8, electronic components other than the light emitting device 12 and the light receiving device 22 are omitted from illustration.

Configuring the interconnect substrate 60 in such a shape as illustrated in FIG. 8 makes it possible to reduce the width of the sensor module 2 while securing the same cross-sectional area for the flow pathway as in the sensor module 1, for example. Namely, use of the flexible interconnect substrate 60 allows a desired shape such as a horizontally elongated shape or a vertically elongated shape to be selected according to required specification.

The sensor module 1 has the function to measure the concentration of a predetermined gas by utilizing changes in the amount of absorbed light, so that the concentration of a gas different from carbon dioxide can be measured by changing the wavelength in use. The sensor module 1 and the like may be used to detect the concentration of acetone contained in a person's breath, for example.

According to at least one embodiment, the size of a sensor module for measuring gas concentration can be reduced.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A sensor module for measuring a concentration of a gas by utilizing changes in an amount of absorbed light, comprising:
    a light emitting device; and
    a light receiving device configured to receive light emitted by the light emitting device,
    wherein the light emitting device and the light receiving device are disposed to face each other across a gap,
    wherein the light emitting device and the light receiving device are positioned such as to be exposed to the gas, and the gap forms part of a flow pathway of the gas, and
    wherein the gap is greater than or equal to 0.2 mm and less than or equal to 1.0 mm,
    wherein the light emitting device is mounted on a first substrate, and the light receiving device is mounted on a second substrate,
    wherein the first substrate and the second substrate are spaced from each other such that the light emitting device and the light receiving device face each other across the gap,
    wherein the first substrate and the second substrate are disposed to face each other and connected via one or more connecting members that are situated farther away from a center of the flow pathway of the gas than are the light emitting device and the light receiving device, and wherein a space surrounded by the first substrate, the second substrate, and the one or more connecting members serves as part of the flow pathway of the gas.

2. The sensor module as claimed in claim 1, wherein the one or more connecting members include one or more intermediate substrates that electrically connect the first substrate and the second substrate.

3. The sensor module as claimed in claim 2, wherein the one or more intermediate substrates includes two L-shaped substrates disposed opposite each other as viewed in a direction normal to the first substrate.

4. The sensor module as claimed in claim 1, wherein a surface of the first substrate on a side where the light emitting device is mounted is covered with a black resist.

5. The sensor module as claimed in claim 1, wherein a surface of the second substrate on a side where the light receiving device is mounted is covered with a black resist.

6. The sensor module as claimed in claim 1, wherein a cross-sectional area of the flow pathway of the gas at a position of the gap is greater than or equal to 80 mm2.

7. The sensor module as claimed in claim 1, wherein the gas is carbon dioxide.

8. The sensor module as claimed in claim 7, wherein a spectrum of the light emitted by the light emitting device includes a wavelength of 4.3 micrometers and has a full width at half maximum of 0.8 micrometers or less.

9. The sensor module as claimed in claim 7, wherein the light receiving device includes a bandpass filter that allows passage of light having a wavelength of 4.3 micrometers.

10. A sensor module for measuring a concentration of a gas by utilizing changes in an amount of absorbed light, comprising:

a light emitting device; and a light receiving device configured to receive light emitted by the light emitting device, wherein the light emitting device and the light receiving device are disposed to face each other across a gap, wherein the light emitting device and the light receiving device are positioned such as to be exposed to the gas, and the gap forms part of a flow pathway of the gas, and wherein the gap is greater than or equal to 0.2 mm and less than or equal to 1.0 mm, wherein the light emitting device and the light receiving device are mounted on a substrate that is flexible, and wherein the substrate is bent such that the light emitting device and the light receiving device face each other across the gap.

* * * * *